US010591360B2

(12) United States Patent
Mainguet et al.

(10) Patent No.: US 10,591,360 B2
(45) Date of Patent: Mar. 17, 2020

(54) THERMAL SENSOR WITH TWO SUPERPOSED PYROELECTRIC PORTIONS FOR MEASURING A CHARGE DIFFERENTIAL

(71) Applicants: COMMISSARIAT A L'ENERGIE ATOMIQUE ET AUX ENERGIES ALTERNATIVES, Paris (FR); IDEMIA IDENTITY & SECURITY FRANCE, Issy les Moulineaux (FR)

(72) Inventors: Jean-Francois Mainguet, Grenoble (FR); Joel Yann Fourre, Marly le Roi (FR)

(73) Assignees: COMMISSARIAT A L'ENERGIE ATOMIQUE ET AUX ENERGIES ALTERNATIVES, Paris (FR); IDEMIA IDENTITY & SECURITY FRANCE, Issy les Moulineaux (FR)

( * ) Notice: Subject to any disclaimer, the term of this patent is extended or adjusted under 35 U.S.C. 154(b) by 54 days.

(21) Appl. No.: 16/041,233

(22) Filed: Jul. 20, 2018

(65) Prior Publication Data

US 2019/0025129 A1 Jan. 24, 2019

(30) Foreign Application Priority Data

Jul. 24, 2017 (FR) ..................................... 17 57000

(51) Int. Cl.
*G01J 5/34* (2006.01)
*A61B 5/1172* (2016.01)
*G06K 9/00* (2006.01)

(52) U.S. Cl.
CPC .............. *G01J 5/34* (2013.01); *A61B 5/1172* (2013.01); *G06K 9/0002* (2013.01)

(58) Field of Classification Search
CPC ......... G01J 5/34; G06K 9/0002; A61B 5/1172
See application file for complete search history.

(56) References Cited

U.S. PATENT DOCUMENTS 4,394,773 A 7/1983 Ruell
6,061,464 A 5/2000 Leger
(Continued)

FOREIGN PATENT DOCUMENTS

EP 2 385 486 A1 11/2011
FR 3 044 407 A1 6/2017
(Continued)

OTHER PUBLICATIONS

U.S. Appl. No. 14/583,967, filed Dec. 29, 2014, 2015/0191309 A1, Jean-Francois Mainguet et al.
(Continued)

*Primary Examiner* — John B Strege
(74) *Attorney, Agent, or Firm* — Oblon, McClelland, Maier & Neustadt, L.L.P.

(57) ABSTRACT

A pyroelectric sensor includes several pixels distributed above a substrate and each pixel includes a first portion made of a pyroelectric material, in direct physical contact with a charge collection electrode, a second portion made of a pyroelectric material, in direct physical contact with a charge collection electrode, the first portion, the second portion and the at least one charge collection electrode being superposed above the substrate, at least one heating element to heat the first and second portions including a pyroelectric material, and an electronic device to measure a difference between charges generated by the first portion including a pyroelectric material and charges generated by the second portion including a pyroelectric material. The pyroelectric sensor makes it possible to suppress a useless part of a
(Continued)

measurement signal. It is particularly advantageous for taking an image of a papillary print.

16 Claims, 4 Drawing Sheets

(56) References Cited

U.S. PATENT DOCUMENTS

| | | | | |
|---|---|---|---|---|
| 7,385,381 | B1 * | 6/2008 | Mainguet | G01D 5/2405<br>324/71.1 |
| 2011/0280276 | A1 * | 11/2011 | Mainguet | G01J 5/024<br>374/102 |
| 2018/0032782 | A1 * | 2/2018 | Mainguet | A61B 5/1172 |
| 2018/0356291 | A1 * | 12/2018 | Mainguet | G01J 5/34 |
| 2019/0148618 | A1 * | 5/2019 | Revaux | H01L 37/02 |

FOREIGN PATENT DOCUMENTS

| | | | |
|---|---|---|---|
| FR | 3 044 408 | A1 | 6/2017 |
| WO | WO 2017/093252 | A1 | 6/2017 |

OTHER PUBLICATIONS

U.S. Appl. No. 14/622,805, filed Jul. 28, 2017, 2018/0032782 A1, Jean-Francois Mainguet et al.
U.S. Appl. No. 14/662,778, filed Jul. 28, 2017, 2018/0032781 A1, Jean-Francois Mainguet et al.
U.S. Appl. No. 15/900,505, filed Feb. 20, 2018, Jean-Francois Mainguet et al.
U.S. Appl. No. 15/922,204, filed Mar. 15, 2018, Jean-Francois Mainguet et al.
Per Client, U.S. Appl. No. 16/064,759, filed Dec. 21, 2016, Unknown.
Per Client, U.S. Appl. No. 15/779,738, filed Nov. 28, 2016, Unknown.
Per Client, U.S. Appl. No. 15/779,787, filed Nov. 28, 2016, Unknown.
U.S. Appl. No. 15/662,805, filed Jul. 28, 2017, 2018/0032782 A1, Jean-Francois Mainguet et al.
U.S. Appl. No. 15/662,778, filed Jul. 28, 2017, 2018/0032781 A1, Jean-Francois Mainguet et al.
French Preliminary Search Report dated Mar. 21, 2018 in French Application 17 57000 filed on Jul. 24, 2017 (with English Translation of Categories of Cited Documents).

* cited by examiner

THERMAL SENSOR WITH TWO SUPERPOSED PYROELECTRIC PORTIONS FOR MEASURING A CHARGE DIFFERENTIAL

TECHNICAL DOMAIN

The invention relates to a thermal patterns sensor, making use of the pyroelectric properties of a material and forming advantageously a papillary print sensor, and particularly a fingerprint sensor.

STATE OF PRIOR ART

In prior art, such a thermal patterns sensor comprises a matrix of pyroelectric capacitors.

Each pyroelectric capacitor comprises a portion made of a pyroelectric material located between a lower electrode and an upper electrode. One electrode is set at a constant potential, and forms a reference electrode. The other electrode collects pyroelectric charges, generated by the pyroelectric material in response to a temperature variation.

Each pyroelectric capacitor thus forms a transducer to translate a variation of the temperature with time into an electric signal such as a difference in electrical potentials.

Such a sensor may for example be of the passive type, making use solely of a difference between a temperature on the thermal pattern to be imaged and a sensor temperature.

In the special case of a papillary print sensor comprising a contact surface on which the print to be imaged will be applied, such a sensor makes use particularly of a difference in temperature between the finger and the contact surface of the sensor. Such a sensor is described for example in U.S. Pat. No. 4,394,773.

The finger is in direct physical contact with the sensor at the ridges of the print. A heat transfer between the skin and the contact surface of the sensor takes place by conduction, which leads to a first variation of the temperature with time.

The finger is not in direct physical contact with the sensor at the valleys of the print. A heat transfer between the skin and the contact surface of the sensor takes place through the air that is rather a thermal insulator, which leads to a second smaller variation of the temperature with time.

The difference between these two variations of the temperature with time results in a difference between the signals measured by the pyroelectric capacitors, depending on whether they are under a valley or under a ridge of the print. Therefore the image of the print shows a contrast that depends on this difference.

After just a few seconds, the temperature of the finger and the temperature of the contact surface of the sensor become homogeneous, and it is no longer possible to obtain a satisfactory contrast.

Another type of sensor, of the active type, offers a solution to this problem through the addition of heating means under the contact surface of the sensor. Such a sensor is described for example in patent application EP 2 385 486 A1.

The heating means dissipate a certain quantity of heat in each pixel of the sensor. Therefore the temperature variation relates to the extent to which this heat quantity is evacuated from the pixel. Therefore the temperature variation is large at the valleys of the print where heat is transferred to the finger only through air, and is smaller at the ridges of the print, where heat is efficiently transferred to the finger by conduction.

Therefore the heating means prevent a thermal equilibrium from being set up between the contact surface of the sensor and the finger. This allows improving the contrast of an image acquired using said sensor, and maintaining it over time.

FIG. 1 diagrammatically illustrates temperature curves as a function of time, in a valley (curve 11) and at a ridge (curve 12) respectively.

The temperature is measured at a time t1 when the heating starts, and at a time t2 after the heating has been active for a certain duration.

A temperature variation $\Delta T1$ is measured in a valley

A temperature variation $\Delta T2$ is measured at a ridge.

The image contrast thus obtained is fairly low.

One purpose of this invention is to provide a pyroelectric sensor, and particularly an active thermal type sensor, providing better contrast than in prior art, and particularly a contrast of more than 20%.

PRESENTATION OF THE INVENTION

This objective is achieved with a thermal patterns sensor of the pyroelectric sensor type comprising a contact surface to apply on it an object to be imaged, particularly a papillary print, and a plurality of pixels distributed between a substrate and said contact surface.

According to the invention, each pixel comprises:

- a first structure, including a first portion comprising a pyroelectric material, said first structure being in direct physical contact with one of the at least one charge collection electrode,
- a second structure, including a second portion comprising a pyroelectric material, said second structure being in direct physical contact with one of the at least one charge collection electrode, the first structure, the second structure and the at least one charge collection electrode being superposed above the substrate;
- at least one heating element, to heat the first and second portions comprising a pyroelectric material; and
- an electronic device connected to the at least one charge collection electrode, and configured to measure a difference between charges generated by one among the first and the second portions comprising a pyroelectric material, and charges generated by the other among the first and second portions comprising a pyroelectric material.

The first and second structures are superposed, and each of these two structures comprises a distinct portion comprising a pyroelectric material.

Thus, one of the portions comprising a pyroelectric material extends on the side of the substrate, while the other of the portions comprising a pyroelectric material extends on the side of the object to be imaged, possibly on the side of a contact surface.

The portion comprising a pyroelectric material that extends on the side of the substrate exchanges little or no heat with the object. It forms a portion called the calibration portion.

When the at least one heating element heats this portion, heat supplied by the heating element is not transferred to the object.

The temperature variation obtained in said portion comprising a pyroelectric material results in the generation of pyroelectric charges called calibration charges, the quantity of which depends simply on heating supplied by the at least one heating element.

These calibration charges are collected by the at least one charge collection electrode.

On the other hand, the portion comprising a pyroelectric material that extends on the side of the object to be imaged exchanges heat with this object. It forms a portion called the measurement portion.

The at least one heating element is located above the substrate. Therefore it is superposed above this substrate, with the first structure, the second structure and the at least one charge collection electrode.

When the at least one heating element heats this portion, heat added by the heating element is transferred to the object more or less efficiently depending on the characteristics of the object. In the case of a print sensor, it is transferred to the finger more or less efficiently depending on whether there is a ridge or valley of the print above the pixel.

The temperature variation obtained in said portion comprising a pyroelectric material results in the generation of pyroelectric charges called measurement charges. Their quantity depends on the heating input by the at least one heating element, and the characteristics of the object to be imaged.

These measurement charges are collected by the at least one charge collection electrode.

By measuring a difference between the measurement charges and the calibration charges (or vice versa), it is possible to obtain ideally a quantity of pyroelectric charges related only to the characteristics of the object to be imaged.

In all cases, a part of the signal that is not useful can be at least partly discarded, which allows improving the contrast of the image of the object.

Said difference in charges is measured, and not calculated. In other words, a lower quantity of charges is directly measured, so that high gain amplifiers can be used in detection without any risk of saturating the signal.

Therefore the sensor obtained is more sensitive, so that pixels can be less heated for active detection which allows therefore consuming less energy, and/or using thicker protection layers to protect the sensor, and/or reducing the duration of temperature variation measurements.

The proposed solution has the advantage that it does not involve the use of lengthy calculations that could make fabrication of the sensor according to the invention more complex.

Furthermore, all pixels of the sensor can be strictly identical, which further simplifies its fabrication.

The proposed solution also provides very high precision, since by construction, calibration data are obtained at the same time as measurement data. This thus avoids any calibration imprecision related to drifts of the sensor over time (for example wear of a contact surface). This also eliminates the effect of heating variations between one measurement and another, such that the invention does not require extremely precise control of heating.

The disclosed solution also provides very high precision because each pixel has its own calibration data. This can thus avoid the effect of differences in the sensitivity of different pixels, for example related to differences in wear and/or heating.

The sensor according to the invention can be said to be "in equilibrium" in that there is an equilibrium of charges to bring them close to zero, which is ideally achieved when no object is touching the sensor.

This equilibrium of charges makes it possible to obtain better use of a digital range of a signal output by the electronic device.

BRIEF DESCRIPTION OF THE DRAWINGS

This invention will be better understood after reading the description of example embodiments given purely for information and that are in no way limitative, with reference to the appended drawings on which.

DETAILED PRESENTATION OF PARTICULAR EMBODIMENTS

The following description is given particularly and non-limitatively in the context of a detection of a papillary print, and particularly a fingerprint.

The invention is not limited to this example of application. The thermal patterns sensor according to the invention can be used to image other types of objects, for example printed circuits.

The thermal patterns sensor according to the invention can also form a mass spectrometer type analysis instrument or a flow meter allowing taking measurements at various depths in an object and studying the response of the object to known heating.

In the following description, the terms "on", "above", "upper", "under", "below", "lower" relate to the orientation of the corresponding figures.

To clarify matters, the (Ox), (Oy) and/or (Oz) axes of an orthonormal coordinate system are shown on some of the figures.

Figure 2:
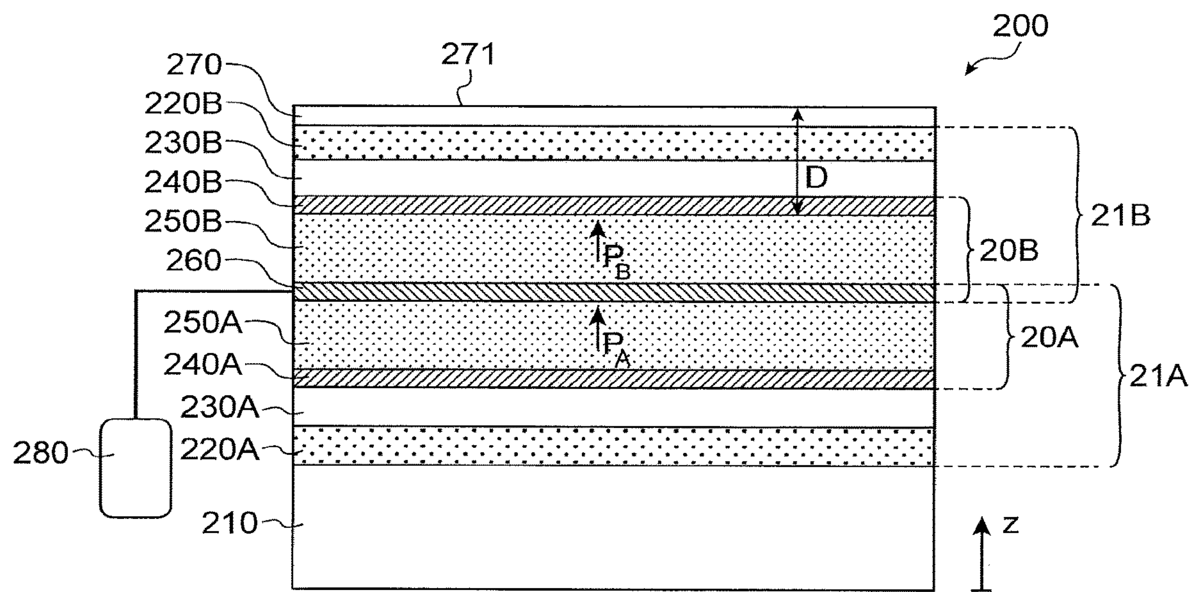
FIG. 2 illustrates a first embodiment of a thermal patterns sensor according to the invention.

FIG. 2 illustrates a first embodiment of a sensor according to the invention.

In particular, this figure shows a pixel 200 of this sensor, the different pixels being formed and distributed in a two-dimensional matrix above a common substrate 210.

For example, the substrate 210 is an ultra-thin plastic or glass substrate, with a thickness for example less than 12 μm. It may also be a substrate made of polyethylene terephthalate (PET) with a thickness of between 100 μm and 150 μm, for example 125 μm.

Each sensor pixel comprises the following, superposed in this order above the substrate 210:

- a first electrical resistor 220A, adapted to be connected to a current or voltage source, and forming a heating element located on the side of the substrate 210;
- a first layer made of a dielectric material 230A, with both electrical insulation and thermal conduction properties;
- a first reference electrode 240A, connected to a constant potential source, preferably to the ground (or chassis ground);
- a first portion 250A comprising a pyroelectric material;
- an electrode 260 called the charge collection electrode;
- a second portion 250B comprising a pyroelectric material;
- a second reference electrode 240B, connected to a constant potential source, preferably to the ground (or chassis ground);

a second layer made of a dielectric material 230B, with both electrical insulation and thermal conduction properties;

a second electric resistor 220B, adapted to be connected to a current or voltage source, and forming a heating element located on the side opposite the substrate 210; and an optional protection layer 270, for example made of DLC ("Diamond-Like Carbon"), to protect the lower layers from repeated contacts with the finger.

The outermost layer of the sensor on the side opposite the substrate forms a contact surface 271 onto which the object to be imaged is applied, in this case the fingerprint of a finger. Said contact surface 271 extends parallel to the Oxy plane.

The distance D along the Oz axis between the contact surface 271 and the upper face of the second portion 250B comprising pyroelectric material is advantageously less than a distribution pitch of sensor pixels (and less than the smallest distribution pitch of sensor pixels, if the pitch along Ox and the pitch along Oy are different from each other).

The first and second reference electrodes can be connected to the same constant potential source.

Throughout the text, when a reference electrode is being described, the term "constant potential source" is used to define a source supplying a potential that remains constant at least for the time between when a read circuit is reset and a time at which said circuit makes a read (read circuit to measure a quantity of charges, and comprising at least the electronic device as described below).

In this case, the second reference electrode 240B also forms electromagnetic shielding to protect the sensor from electrostatic parasites, particularly at around 50 Hz, introduced by contact with the skin when the finger touches the contact surface of the sensor. In order to optimise this shielding, the second reference electrode 240B extends in a single piece without openings above the substrate, passing through all the pixels of the sensor.

The first portion 250A comprising a pyroelectric material in this case extends in direct physical contact with the first reference electrode 240A on the lower side, and with the charge collection electrode 260 on the upper side.

One or several intercalated electricity conducting layers may possibly be inserted between said first portion 250A and the charge collection electrode 260, and/or between said first portion 250A and the first reference electrode 240A. We define herein a first structure including at least the first portion 250A comprising a pyroelectric material and possibly this or these intercalated layer(s).

The first structure, the first reference electrode 240A and the charge collection electrode 260 together form a first pyroelectric capacitor 20A located on the side of the substrate.

In the same way, the second portion 250B comprising a pyroelectric material in this case extends in direct physical contact with the charge collector electrode 260 on the lower side, and with the second reference electrode 240B on the upper side.

One or several intercalated electricity conducting layers may possibly be inserted between said second portion 250B and the charge collection electrode 260, and/or between said second portion 250B and the second reference electrode 240B. We define herein a second structure including at least the second portion 250B comprising a pyroelectric material and possibly this or these intercalated layer(s).

The second structure, the second reference electrode 240B and the charge collection electrode 260 together form a second pyroelectric capacitor 20B located on the side of the contact surface 271.

Therefore the charge collection electrode 260 is common to the two pyroelectric capacitors 20A, 20B.

The first pyroelectric capacitor 20A is heated by the first electrical resistor 220A, through the first layer of dielectric material 230A, for implementation of an active type detection.

The first pyroelectric capacitor 20A, the first electrical resistor 220A, and the first layer made of a dielectric material 230A together form a first thermal detection cell 21A, located on the same side as the substrate.

Similarly, the second pyroelectric capacitor 20B is heated by the second electrical resistor 220B, through the second layer of dielectric material 230B, for implementation of an active type detection.

The second pyroelectric capacitor 20B, the second electrical resistor 220B, and the second layer made of a dielectric material 230B together form a second thermal detection cell 21B located on the same side as the contact surface, and superposed on the first cell 21A.

The layout of these two cells 21A, 21B is symmetric relative to a plane parallel to the contact surface of the sensor, in this case passing through the charge collection electrode 260.

In particular, in this case the dimensions and compositions of the different components of each cell 21A, 21B are identical in pairs. More specifically, the two portions 250A, 250B comprising a pyroelectric material have the same thickness (dimension along the z axis) and the same composition. In particular, they may be composed of the same material or mix of materials.

Thus, the thermal resistance between the first electrical resistor 220A and the first portion 250A is equal to the thermal resistance between the second electrical resistor 220B and the second portion 250B.

Furthermore, the same current passes through the first electrical resistor 220A and the second electrical resistor 220B, such that the same quantity of heat is supplied to the first and second portions respectively comprising a pyroelectric material.

The first thermal detection cell 21A located on the same side as the substrate is not much or not at all affected by heat exchanges with an object bearing on the contact surface 271 of the sensor. Thus, activation of the first electrical resistor 220A creates a temperature change $\Delta T_A$ in the layer 250A, that does not depend on or only slightly depends on the characteristics of the object bearing on the contact surface 271. It depends on the thermal characteristics of the substrate and its lower layers, if any, assumed to be homogeneous over the entire sensor. Therefore the temperature variation $\Delta T_A$ is the same, regardless of whether there is a ridge or a valley of a fingerprint above the pixel 200 at the contact surface 271. The first cell 21A thus forms a calibration cell.

On the contrary, the second thermal detection cell 21B located on the same side as the contact surface 271 is strongly affected by heat exchanges with an object bearing on the contact surface 271 of the sensor. Activation of the second electrical resistor 2206 creates a temperature change $\Delta T_B$ that is closely dependent on the characteristics of the object bearing on the contact surface 271. Therefore the temperature variation $\Delta T_B$ is different depending on whether there is a ridge or a valley of a fingerprint above the sensor pixel at the contact surface 271. The second cell 21B thus forms a measurement cell.

At the calibration cell 21A, the temperature variation $\Delta T_A$ entrains the generation of first pyroelectric charges called calibration charges, the quantity of which is directly dependent on $\Delta T_A$ (the number of charges generated is proportional to the temperature variation).

At the measurement cell 21B, the temperature variation $\Delta T_B$ entrains the generation of second pyroelectric charges called measurement charges, the quantity of which is directly dependent on $\Delta T_B$.

Consequently, only the quantity of measurement charges varies, depending on whether there is a ridge or a valley of a print above the pixel.

Only the variation of this quantity of charges is useful to image the print.

Therefore, a distinction among measurement charges is made between so-called useful charges for which the quantity varies depending on whether there is a ridge or a valley of a print above the pixel, the other charges being said to be useless.

The idea of the invention is to subtract calibration charges from measurement charges (or vice versa) to be as free as possible from these so-called useless charges.

Figure 1:
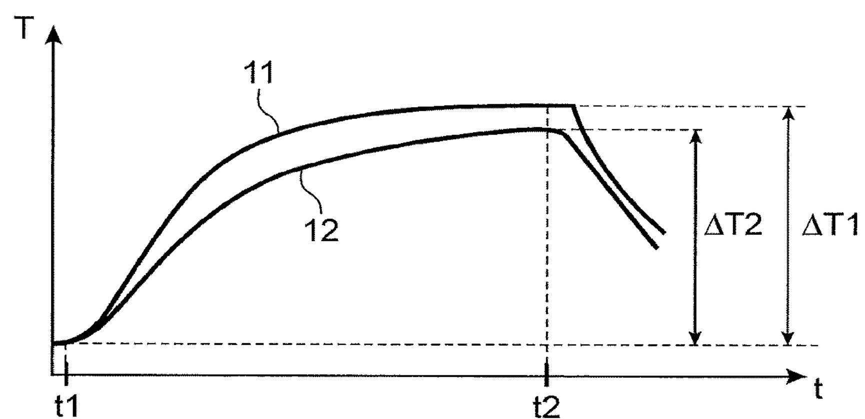
FIG. 1 diagrammatically illustrates temperature curves in an active thermal type print sensor.

Referring once again to FIG. 1, the objective is to at least partly eliminate the influence of signal portions located under the curve 12. In other words, rather than measuring a large temperature variation ΔT1 or ΔT2 by making measurements of charge quantities, small temperature variations are measured, close to the difference between £T1 and ΔT2.

For example, it is possible to eliminate the influence of signal portions located under the curve 12 in their entirety by combining the charges $\Delta T_A$ and $\Delta T_B$. A zero variation or a variation equal to the difference between ΔT1 and ΔT2, depending on whether there is a ridge or a valley above the pixel, is then measured by making measurements of the charge quantity.

It is even possible to subtract a little more than the useless charges so as to measure a positive or negative charge variation depending on whether there is a ridge or a valley above the pixel.

In other words, different calibration types can be used, for example to delete only part or all of a useless part of a signal, or in other words to subtract the required quantity of calibration charges.

The quantity of charges subtracted can be adjusted by an appropriate choice, on the side of cell 21A, of the thermal characteristics of the substrate and lower layer(s) if any, and/or the quantity of heat injected by the resistor 220A, the pyroelectric characteristics of the first portion 250A, and/or the thickness of the first portion 250A, relative to the equivalent characteristics on the side of the cell 21B.

The following gives details for the different parameters that can be adjusted to subtract the required quantity of calibration charges.

In all cases, the amplitude of the largest measured signal variation is very much reduced, in comparison with a difference between a signal corresponding to ridges and a signal corresponding to valleys, such that the contrast is increased.

In the first embodiment illustrated herein, the charges are subtracted directly at the charge collection electrode 260, in this case common to the calibration cell 21A and the measurement cell 21B.

The two portions 250A, 250B comprising a pyroelectric material are polarised along the $P_A$ and $P_B$ axes respectively.

The $P_A$ and $P_B$ axes are oriented along the same axis, in this case parallel to the z axis, in which the z axis is an axis orthogonal to the contact surface 271 of the sensor.

Furthermore, the $P_A$ and $P_B$ axes are oriented in the same direction (from bottom to top, or from top to bottom).

Thus, and due to symmetry between the calibration cell 21A and the measurement cell 21B, and the central position of the charge collection electrode 260, the measurement charges $\Delta T_B$ and the calibration charges $\Delta T_A$, all collected at the charge collection electrode 260, have opposite signs. Thus, charges are subtracted by adding positive charges and negative charges.

The charge collection electrode 260 is connected to an electronic device 280, configured to measure a quantity of charges. Therefore the electronic device 280 directly measures a quantity of charges corresponding to the difference between charges generated in the measurement cell 21B, by the second portion 250B comprising a pyroelectric material, and charges generated in the calibration cell 21A, by the first portion 250A comprising a pyroelectric material (or vice versa).

The electronic device 280 is a known device such as those of the pyroelectric sensors according to prior art. In particular, the electronic device 280 can measure charge quantities by reading voltages or current.

In order to optimise calibration performances, it is preferable to maximise thermal insulation between two portions 250A, 250B comprising a pyroelectric material.

Therefore this pyroelectric material is advantageously based on PVDF (polyvinylidene fluoride), that is a good thermal insulator. However other pyroelectric materials cannot be excluded, for example such as AlN (aluminium nitride). The first and second portions 250A, 250B may be composed entirely of a pyroelectric material, or they may be composed of several materials, at least one of which is pyroelectric.

An electricity conducting element located between these two portions of pyroelectric material, in this case the charge collection electrode 260, can also have thermal insulation properties. This conducting element may for example be made of PEDOT:PSS (mix of two polymers: poly(3,4-ethylenedioxythiophene) and polystyrenesulphonate).

According to one variant not shown, the layer 260 common to cells 21A and 21B is duplicated in two layers 260A, 260B between which a thermal insulation layer extends. The two layers 260A, 260B are connected to each other electrically, for example through vias passing through said thermal insulation layer. The vias can be distributed over the entire surface of the sensor, or only at the border of the pixel matrix.

According to another variant, the substrate 210 is made of silicon. A layer of an electrically insulating material is then intercalated between each electrical resistor 220A and the substrate 210. This intercalated layer advantageously also has a high thermal resistance to limit the influence of silicon that is an excellent thermal conductor.

Figure 3:
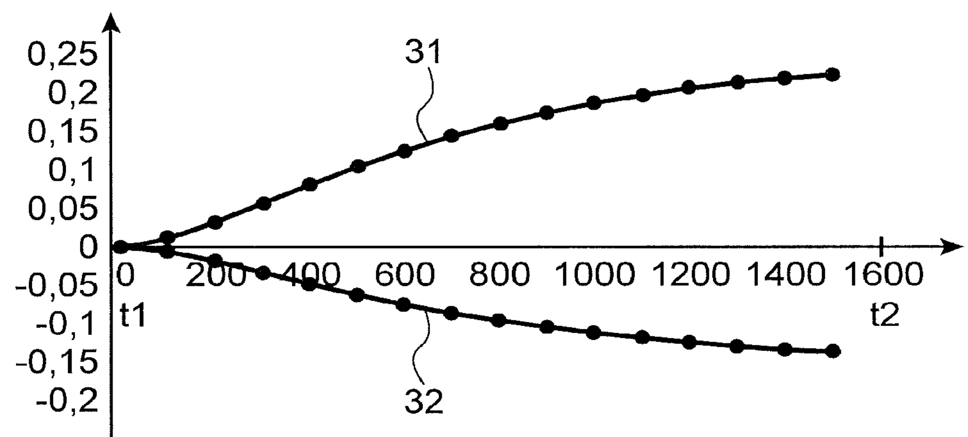
FIG. 3 diagrammatically illustrates temperature curves in a thermal patterns sensor according to the invention.

FIG. 3 illustrates curves of the quantity of charges measured at the charge collection electrode (in arbitrary units) as a function of time (in μs).

Curve 31 corresponds to the case in which there is a valley of a print above the pixel.

Curve 32 corresponds to the case in which there is a ridge of a print above the pixel.

At time t1=0, heating by the first and second electrical resistors 220A, 220B is started. This heating remains active until t2=1600 μs.

In this case, the sensor is configured so that the calibration cell generates a charge quantity so as to measure a positive or negative variation of charges, depending on whether there is a ridge or a valley of a print above the pixel.

The curve 31 changes from a null value to the value of 0.25.

The curve 32 changes from a null value to the value of −0.15.

The corresponding contrast is 100%.

Figure 4:
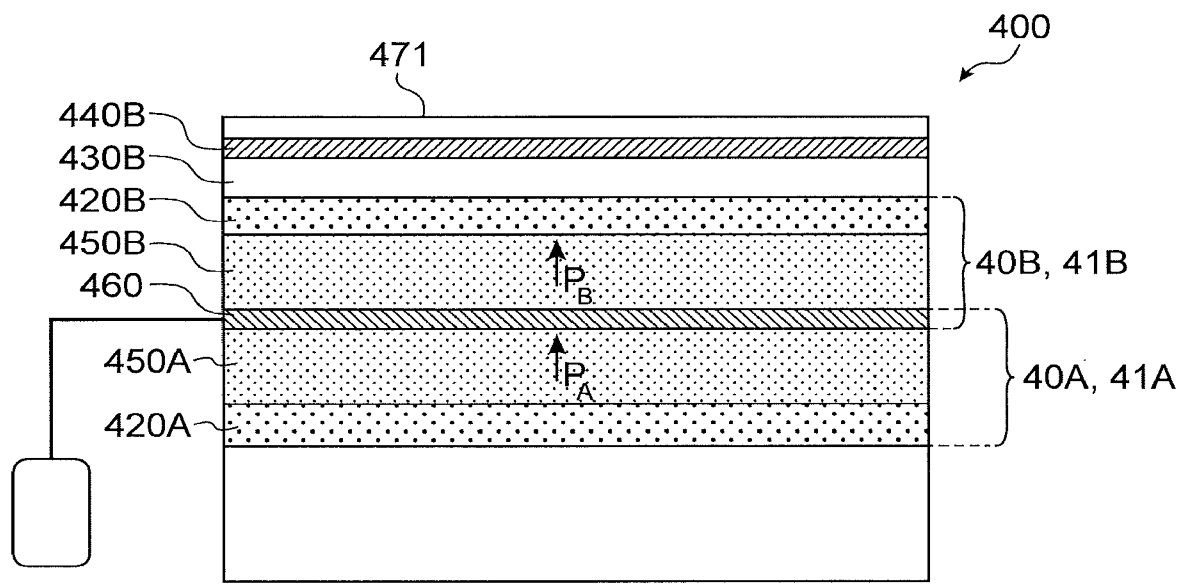
FIG. 4 illustrates a variant of the first embodiment of a thermal patterns sensor according to the invention.

FIG. 4 illustrates a variant of the sensor illustrated in FIG. 2.

The only difference between this variant and the sensor illustrated in FIG. 2 is that the pixels 400 do not have any reference electrode(s) distinct from a heating element.

In particular, a single element 420A or 420B forms a heating element and also a reference electrode, for the first or second thermal detection cell respectively.

This element is composed of an electrical resistor 420A or 420B respectively, connected to a constant potential source that can alternatively take a null value and a non-null value.

The electrical resistor 420A, 420B then forms a heating element, that is activated when this potential is equal to a non-null value.

It also forms a reference electrode for a first and second pyroelectric capacitor 40A, 40B respectively, since it is connected to a constant potential source.

The sensor is thus simplified since, in each calibration cell, the assembly composed of a heating element, an electrically insulating layer and a reference electrode, is replaced by this single element 420A or 420B respectively. Thus, the calibration cell 41A corresponds directly to the first pyroelectric capacitor 40A, and the measurement cell 41B corresponds directly to the second pyroelectric capacitor 40B.

This variant takes advantage of the fact that a reference electrode and a heating electrode can both be composed of the same material.

The sensor according to this variant has a shielding layer 440B that extends between the contact surface 471 and the measurement cell 41B, to protect the sensor from electrostatic parasites, particularly around 50 Hz. This shielding layer 440B is an electrical conductor, and is electrically insulated from the second electrical resistor 420B by a layer made of a dielectric material 430B having both electrical insulation and thermal conductivity properties. It preferably extends in a single piece without openings above the substrate, passing through all the pixels of the sensor.

According to another variant, not shown, the sensor according to the invention does not have any electromagnetic shielding. Since the measurement cell and the calibration cell of a same pixel are subject to the same disturbances, and since the equivalent of a charge differential is measured, it can be expected that the charges generated by these disturbances will cancel out so that such a shielding is no longer necessary. In practice, it is difficult to achieve this noise cancellation. The sensor may then comprise non-polarised pixels to measure and subtract a disturbance common to the entire sensor (noise in common mode of the pixels matrix).

We will now describe a second embodiment of the invention in which charges are not subtracted by the addition of positive and negative charges at a common electrode, but by differential measurement from signals collected by two distinct electrodes.

This second embodiment is particularly advantageous on a silicon substrate, on which it is easier to multiply a number of electrical connections.

Only the differences between this embodiment and the first embodiment will be described.

Figure 5:
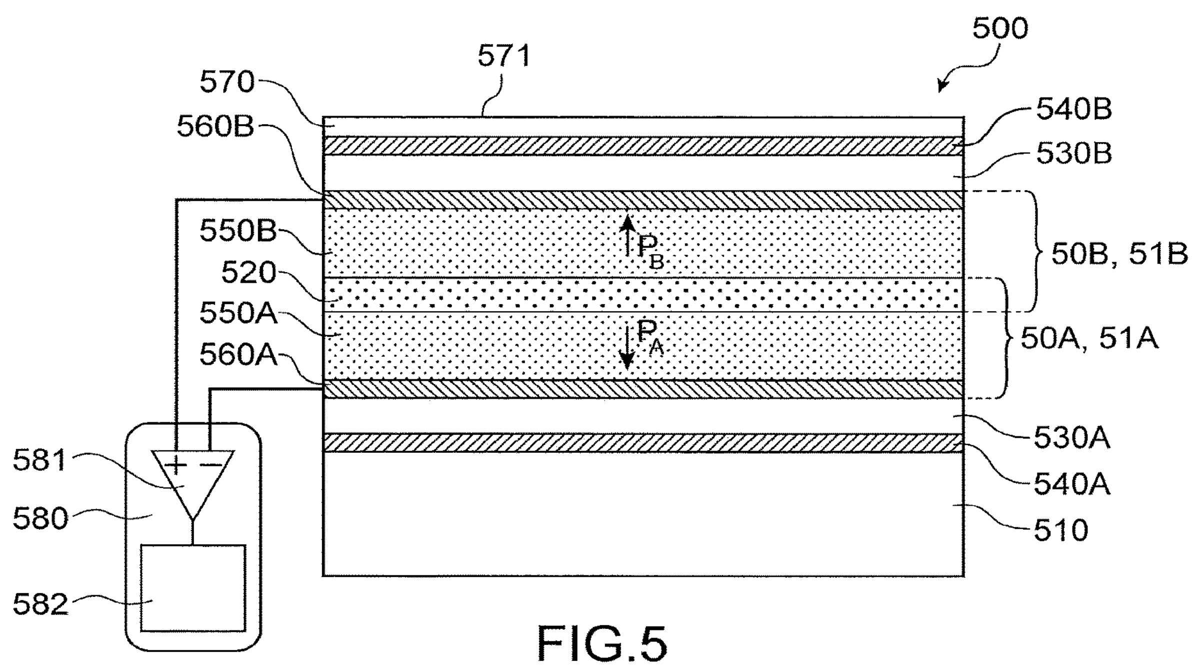
FIGS. 5 to 7 diagrammatically illustrate three variants of a second embodiment of a thermal patterns sensor according to the invention.

According to a first variant illustrated on FIG. 5, each pixel 500 of the sensor comprises the following, superposed in this order above the substrate 510:

- a first conducting layer 540A, connected to a constant potential source, for example to the ground (or chassis ground);
- a first layer made of a dielectric material 530A;
- a first charge collection electrode 560A;
- a first portion 550A comprising a pyroelectric material;
- a central electrode 520, connected to a constant potential source that can alternatively take a null value and a non-null value, forming a reference electrode and also a heating element activated when this potential takes a non-null value;
- a second portion 5506 comprising a pyroelectric material;
- a second charge collection electrode 560B;
- a second layer made of a dielectric material 5306;
- a second conducting layer 540B connected to a constant potential source, for example the ground (or chassis ground), forming electromagnetic shielding to protect the sensor; and
- an optional protection layer 570, as described above.

In order to optimise the shielding, the second conducting layer 5406 extends in a single piece without openings above the substrate, passing through all the pixels of the sensor.

As shown in FIG. 4, this variant takes advantage of the fact that a reference electrode and a heating electrode can both be composed of the same material. In this case, the central electrode 520 forms a reference electrode and also a heating element.

In this case, the first portion comprising a pyroelectric material 550A extends in direct physical contact with the first charge collection electrode 560A on the lower side, and with the central electrode 520 on the upper side.

As before, one or several intercalated electricity conducting layers may be inserted between said first portion 550A and the central electrode 520, and/or between the first portion 550A and the first charge collection electrode 560A. We define a first structure comprising at least the first portion 550A, and possibly this or these intercalated layer(s).

Said first structure, the first charge collection electrode 560A and the central electrode 520 together form a first pyroelectric capacitor 50A located on the side of the substrate.

In the same way, in this case the second portion 550B extends in direct physical contact with the central electrode 520 on the lower side and with the second charge collection electrode 560B on the upper side.

One or several intercalated electricity conducting layers may be inserted between the second portion 550B and the central electrode 520, and/or between the second portion 550B and the second charge collection electrode 560B. We define a second structure comprising at least the second portion 550B, and possibly this or these intercalated layer(s).

Said second structure, the central electrode 520 and the second charge collection electrode 560B together form a second pyroelectric capacitor 50B located on the side of the contact surface 571.

The two pyroelectric capacitors 50A, 50B can be heated by the central electrode 520, for implementation of an active type detection. Therefore, by construction, heating is symmetric in the two pyroelectric capacitors 50A, 50B.

As in FIG. 4, a first thermal detection cell 51A, comprising the first pyroelectric capacitor 50A and its heating element 520, correspond directly to the first pyroelectric capacitor 50A.

Similarly, a second thermal detection cell 51B, comprising the second pyroelectric capacitor 50B and its heating element 520, corresponds directly to said second pyroelectric capacitor 50B.

As before, the layout of the two cells 51A, 51B is symmetric about a plane parallel to the contact surface of the sensor, in this case passing through the central electrode 520.

The first cell 51A, located on the substrate side, forms a calibration cell as described above.

The second thermal detection cell 51B, located on the side of the contact surface 571, forms a measurement cell like that described above.

As before, the objective is to subtract pyroelectric calibration charges generated in the calibration cell 51A, from pyroelectric measurement charges generated in the measurement cell 51B (or vice versa).

In this case, the calibration charges are collected by the first charge collection electrode 560A, while the measurement charges are collected by the second charge collection electrode 560B.

As before, the polarisation axes $P_A$ and $P_B$ of portions 550A, 550B comprising a pyroelectric material are oriented parallel to the z axis. On the other hand, in this case these axes are oriented in opposite directions (both towards the central electrode or both towards the corresponding charge collection electrode).

Therefore measurement charges and calibration charges are the same sign (positive or negative). Therefore the subtraction of charges is made at an electronic device 580 connected to the two charge collection electrodes 560A, 560B.

In this case, the electronic device 580 comprises a differential amplifier 581 with its input connected firstly to the first charge collection electrode 560A and secondly to the second charge collection electrode 560B, with its output providing a differential signal corresponding to the difference between the two input signals. The differential amplifier 581 is then connected to an electronic device 582 providing an output voltage, or a digital value directly if it contains an analogue-digital converter, which is function of the difference between the measurement charges and the calibration charges (or vice versa).

As before, an electricity conducting element located between the two portions of pyroelectric material, in this case the common electrode 520, can have thermal insulating properties (in particular it can be made of PEDOT:PSS).

It will be noted that there is no need for the pixel to have electromagnetic shielding on the side of the substrate. Consequently, the first conducting layer 540A simply improves the symmetry of the pixel.

Figure 6:
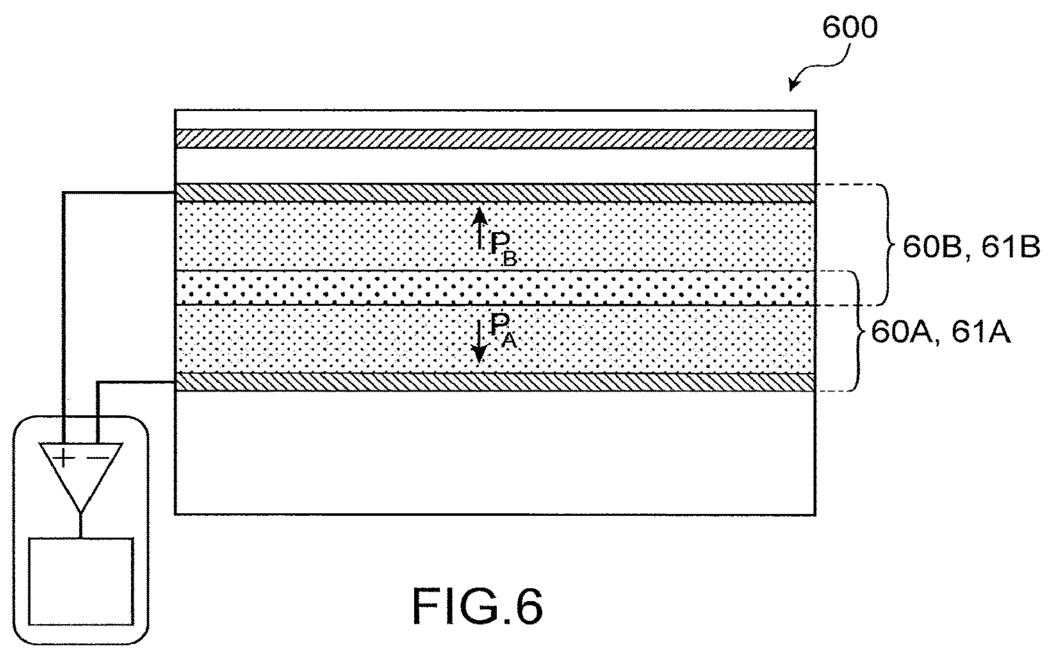

The inventors have demonstrated that it is possible to manage without this first conducting layer 540A (and the first layer of a dielectric material 530A), since the associated lack of symmetry is negligible, or can be compensated by other means (see below). This variant is illustrated in FIG. 6, on which the numeric references correspond to those shown on FIG. 5, the first digit being replaced by a 6.

According to another variant, not shown, the sensor according to the invention does not have the second conducting layer 540B forming an electromagnetic shielding layer. It can be expected indeed that noise sources disturb the two pyroelectric capacitors 60A, 60B in the same way (in particular noise injected by the heating system). In this case, the noise effect is cancelled by the differential measurement, and there is no need for an electromagnetic shielding layer.

According to another variant, not shown, the measurement cell and the calibration cell each comprise a distinct resistor forming both the reference electrode and the heating element, the two distinct resistors being arranged between the two portions comprising a pyroelectric material.

Figure 7:
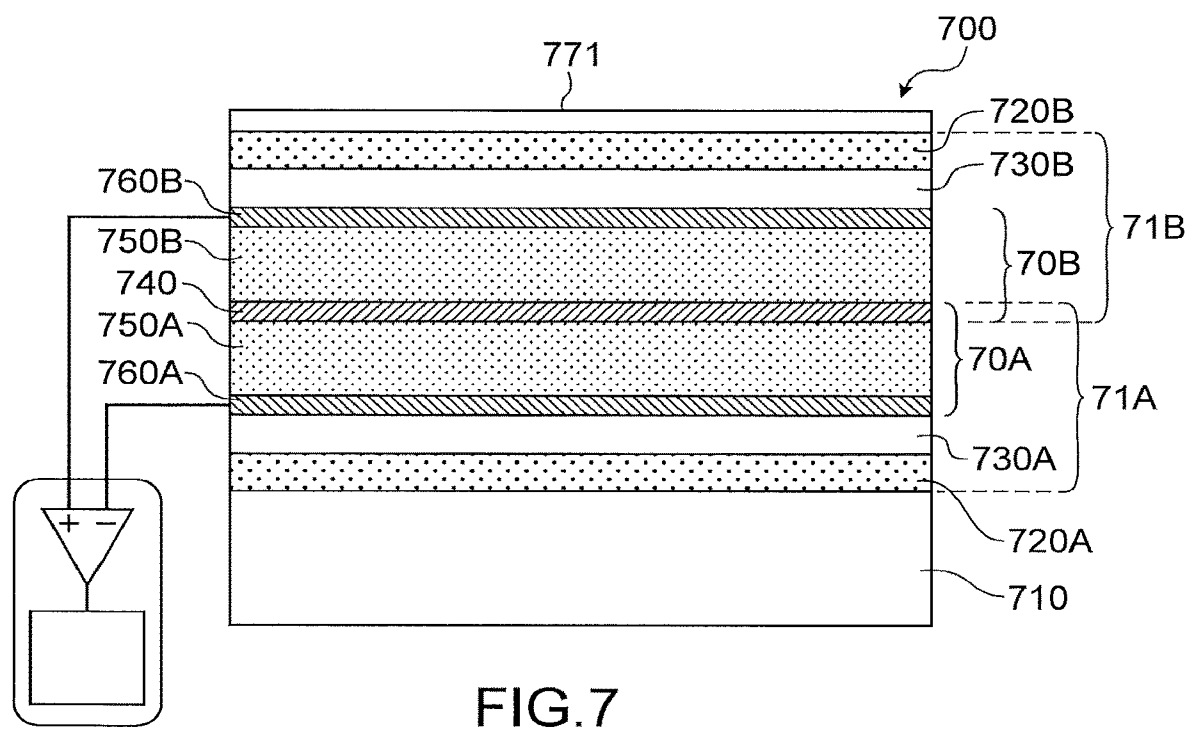

According to another variant illustrated on FIG. 7, heating is not supplied by a central element located between the two portions comprising a dielectric material, but rather by two distinct elements located symmetrically on each side of these two portions.

In particular, the pixel 700 comprises:

a first electrical resistor 720A located between the substrate 710 and the first charge collection electrode 760A, adapted to be connected to a current or voltage source, and forming a heating element located on the side of the substrate 710; and a second electrical resistor 720B located between the second charge collection 760B and the contact surface 771, adapted to be connected to a current or voltage source, and forming a heating element located on the side of the contact surface 771.

Each electrical resistor 720A, 720B is separated from the neighbouring charge collection electrode 760A, 760B respectively by a layer made of a dielectric material 730A, 7308 respectively.

Once again, a first pyroelectric capacitor 70A, and a second pyroelectric capacitor 70B can be defined, in this case sharing a central electrode reference 740.

The first pyroelectric capacitor 70A with the first electrical resistor 720A and the first layer made of a dielectric material 730A, forms a calibration cell 71A.

The second pyroelectric capacitor 70B with the second electrical resistor 720B and the second layer made of a dielectric material 730B, forms a measurement cell 71B.

According to this variant, the central electrode 740, acts only as a common reference electrode for the two pyroelectric capacitors 70A, 70B.

Since the two pyroelectric capacitors 70A, 70B are connected to the same differential amplifier, and are arranged to be symmetric with one above the other, this central electrode can be suppressed (variant not shown). Each pixel then has no reference electrode located between the first and the second structures.

In this case, the first and second portions 750A and 750B respectively are not separated from each other by a conducting layer connected to a constant potential source. They can extend in direct physical contact with each other, or on each side of a layer of a glue layer electrically conducting but not connected during operation.

Figure 8:
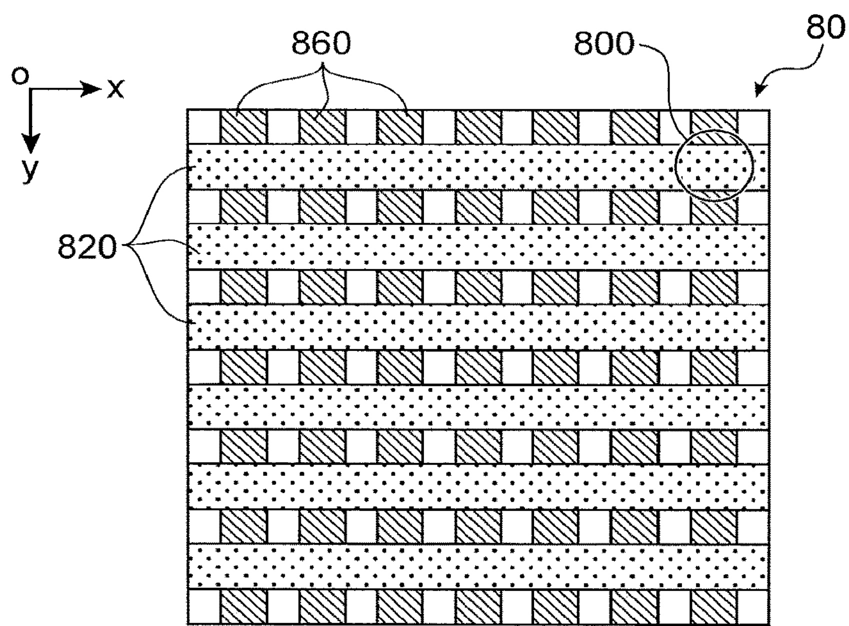
FIG. 8 is a top view diagrammatically illustrating an advantageous arrangement of charge collection electrodes and heating elements in a thermal patterns sensor according to the invention.

FIG. 8 is a top view diagrammatically illustrating an advantageous arrangement of charge collection electrodes and heating elements in a sensor 80 according to the invention.

According to this arrangement, the charge collection electrodes 860 extend in a series of strips parallel to each other when each of the pixels comprises a common charge collection electrode (first embodiment), or in two series of strips parallel to each other when each of the pixels comprises two charge collection electrodes (second embodiment). When the electrodes 860 extend along two series of strips, the strips are superposed in pairs above the substrate.

Each series of strips extends in a plane parallel to the plane of the contact surface of the sensor.

Similarly, the heating elements 820 extend in two series of strips parallel to each other when each of the pixels comprises two heating elements (FIGS. 2, 4, 7), or in one series of strips parallel to each other when each of the pixels comprises a common heating element (FIGS. 5 and 6). When the heating elements 820 extend along two series of strips, the strips are superposed in pairs above the substrate. In other words, the heating elements in the form of a strip are then arranged facing each other in pairs. Each heating element in the form of a strip can be simply called a "heating strip".

Each series of strips extends in a plane parallel to the plane of the contact surface of the sensor.

The heating elements 820 and the electrodes 860 extend along cross-directions, preferably orthogonal to each other.

Each pixel 800 corresponds to an intersection region, as seen in a top view, between an electrode 860 (or two superposed electrodes), and a heating element 820 (or two superposed elements). The pixel concerned can be precisely identified when reading a charge collection electrode, knowing which heating element is active.

The matrix of pixels thus forms a passive matrix, which has the advantage of requiring a smaller number of electrical connections. This advantage is particularly interesting in the second embodiment in which each pixel comprises two charge collection electrodes.

In this case, each heating strip can be connected in series or in parallel to the facing heating strip, such that two facing heating strips are connected to the same current or voltage source.

They can also both have the same dimensions and the same composition, such that they form the same resistance and supply the same heating.

The invention is not limited to this arrangement. The pixel matrix of the sensor according to the invention may for example form an active matrix in which each of the charge collection electrodes of each pixel are distinct from each other, and are individually connected to electronic measurement devices.

In order to optimise the calibration used, different adjustment solutions may be used to subtract the required quantity of calibration charges.

In particular, at least one parameter related to an upper region of the pixel including the measurement cell is adjusted, relative to the corresponding parameter on a lower region of the pixel including the calibration cell, so as to subtract the required quantity of calibration charges.

This adjustment can be made by differentiated heating of the two portions comprising a pyroelectric material.

Such an adjustment is adapted when the measurement cell and the calibration cell have heating elements distinct from each other.

For example, the electrical resistance of the heating element associated with one cell is adjusted relative to the electrical resistance of the heating element associated with the other cell.

These two heating elements can then have different shapes (for example different thicknesses and/or lengths).

However, the same current can pass through them.

For example, the sensor according to the invention may comprising heating strips superposed in pairs (see FIG. 8), each heating strip and the heating strip facing it being connected together in series or in parallel, the dimensions of each strip being different.

In particular, the shape and dimensions of each heating strip may be different from the shape and dimensions of the heating strip facing it, such that the difference between the charges generated by the first portion made of a pyroelectric material and the charges generated by the second portion made of a pyroelectric material in the same pixel is zero when the sensor is in direct physical contact with air on the side opposite the substrate.

However, such an adjustment has the disadvantage that it is static.

As a variant, an adjustment by heating can be obtained by injecting different values of current or voltage into the two heating elements of one and the same pixel.

Such an adjustment can be implemented in real time and adapted to real operating conditions.

It can also reduce the electricity consumption of the sensor by minimising thermal losses to the substrate, these low thermal losses being compensated by heating the substrate side less than the contact surface side.

For example, the sensor according to the invention may comprise heating strips superposed in pairs (see FIG. 8), each heating strip and the heating strip facing it not being connected together, such that different values of current can pass through each.

In particular, the current injected into one heating strip and the current injected into the heating strip facing it can be adjusted such that the difference between charges generated by the first portion made of a pyroelectric material and charges generated by the second portion made of a pyroelectric material in the same pixel is zero when the sensor is in direct physical contact with air on the side opposite the substrate, and for a predetermined integration time (duration associated with the temperature variations considered).

The adjustment can also be made at two portions comprising a pyroelectric material.

In particular, the following can be adjusted:

- the pyroelectric coefficient of one portion comprising a pyroelectric material, relative to the pyroelectric coefficient of the other portion comprising a pyroelectric material (by not polarising them exactly alike, or using two different materials); and/or
- the thickness of one portion comprising a pyroelectric material, relative to the thickness of the other portion comprising a pyroelectric material (knowing that the charges generated by each of said portions do not depend on the thickness, but the temperature rise will be different).

Finally, the adjustment can also be made by an appropriate choice of materials and thicknesses for the different parts forming a pixel of the sensor.

In particular, the thermal characteristics of the different layers comprising a pixel of the sensor according to the invention, particularly thermal conduction and capacitances, are adjusted.

These magnitudes depend on the nature and the thicknesses of the materials.

Since the layers forming the measurement cell and the layers forming the calibration cell are preferably symmetrical with each other, such an adjustment is preferably implemented by adjusting the thermal characteristics of the substrate.

For example, the sensor can be configured such that heat transfers between the first portion comprising a pyroelectric material and the substrate correspond approximately to heat transfers between the second portion comprising a pyroelectric material and a ridge of a print (when the print is bearing on the contact surface of the sensor). The thermal characteristics of skin can assumed to be approximately the same as those of water. A substrate is then chosen with approximately the same thermal conduction as water (assuming that the thermal effect of the protection layer is negligible).

According to another variant, the sensor according to the invention can be configured such that heat transfers between the first portion comprising a pyroelectric material and the substrate are less than heat transfers between the second portion comprising a pyroelectric material and a ridge of a print, and more than heat transfers between the second portion comprising a pyroelectric material and a valley of a print (when the print is bearing on the contact surface of the sensor).

A substrate is then chosen with thermal conduction between the thermal conductions of water and of air.

This adjustment by the thermal characteristics may also take account of the thermal characteristics of intermediate layers located between the measurement cell and the contact surface and/or between the calibration cell and the substrate, for example the thermal characteristics of a protection layer.

Preferably, such an adjustment also takes account of the thermal characteristics of a support on which the substrate lies, during use.

The different adjustment solutions mentioned above can be combined with each other.

It will be noted that the adjustment results in a slight loss of symmetry between a measurement cell and the corresponding calibration cell (at the heating, or at the structure of the sensor).

The man skilled in the art will know how to dimension a sensor according to the invention providing the required calibration, notably using simulations.

In particular, the composition and the thickness of the different elements composing a pixel of the sensor may be adapted such that the difference between the charges generated by the first portion made of a pyroelectric material and the charges generated by the second portion made of a pyroelectric material of the same pixel is zero when the sensor is in direct physical contact with air on the side opposite the substrate.

In each embodiment, there is some symmetry between an upper region (on the side of the contact surface) and a lower region (on the side of the substrate) of the pixel. Furthermore, the arrangement of the pixel enables approximately symmetric heating of these two regions, by a central heating element or by two heating elements.

The invention is not limited to the examples described, many other variants could be used, to define two superposed pyroelectric cells each implementing an active type thermal detection.

It will be noted that in most cases, each pixel of the sensor according to the invention comprises two superposed pyroelectric capacitors, each containing a portion comprising a pyroelectric material, a charge collection electrode, and a reference electrode. The two pyroelectric capacitors can share the same charge collection electrode or the same reference electrode.

For example, in each pixel, an electrically conducting thermal insulation layer may be located between the first and the second portions comprising a pyroelectric material.

Furthermore, the idea of the invention can be adapted to an image capture using a matrix of thermistors (resistive element with an electrical resistance that varies as a function of the temperature). Each pixel of the sensor then has two vertically superposed thermistors, one dedicated to measurement and the other dedicated to calibration. These two thermistors are preferably separated by a thermally insulating layer. The signals measured respectively on the measurement thermistor and on the calibration thermistor are then subtracted. This can be done for example by polarising said two thermistors, installed in series, with a known potential, and reading a potential between these two thermistors. According to one advantageous variant, a difference between this potential between the two thermistors and a potential between two reference thermistors, is measured.

The invention claimed is:

1. A thermal patterns sensor of a pyroelectric sensor type, comprising a contact surface to apply on it an object to be imaged and a plurality of pixels distributed between a substrate and said contact surface, wherein each pixel comprises:

at least one charge collection electrode;

a first structure, including a first portion comprising a pyroelectric material, said first structure being in direct physical contact with one of the at least one charge collection electrode;

a second structure, including a second portion comprising a pyroelectric material, said second structure being in direct physical contact with one of the at least one charge collection electrode, wherein the first structure, the second structure and the at least one charge collection electrode are superposed above the substrate;

at least one heating element to heat the first and second portions comprising a pyroelectric material; and an electronic device connected to the at least one charge collection electrode, and configured to measure a difference between charges generated by one among the first and the second portions comprising a pyroelectric material, and charges generated by the other among the first and second portions comprising a pyroelectric material.

2. The sensor according to claim 1, wherein the first portion comprising a pyroelectric material and the second portion comprising a pyroelectric material have the same thickness and the same chemical composition.

3. The sensor according to claim 1, wherein each pixel comprises two superposed pyroelectric capacitors, each including a portion comprising a pyroelectric material, a charge collection electrode, and a reference electrode, with the two pyroelectric capacitors sharing the same collection electrode or the same reference electrode.

4. The sensor according to claim 1, wherein the first and second structures are each in direct physical contact with the same charge collection electrode, called the common electrode, located between the first and the second structures.

5. The sensor according to claim 4, wherein each of the first and second portions comprising a pyroelectric material have a respective polarisation, the polarisations being oriented along the same axis and in the same direction.

6. The sensor according to claim 4, wherein said electronic device is configured to measure charges collected by said common electrode.

7. The sensor according to claim 4, wherein each pixel further comprises two reference electrodes, located on each side of a stack comprising the first structure, the common electrode and the second structure.

8. The sensor according to claim 1, wherein the first structure and the second structure are each in direct physical contact with two respective charge collection electrodes, one being located on one side of a stack including the first and second structures, and the other being located on the other side of this stack.

9. The sensor according to claim 8, wherein each of the first and second portions comprising a pyroelectric material have a respective polarisation, the polarisations being oriented along opposite directions.

10. The sensor according to claim 8, wherein said electronic device comprises a differential amplifier, connected at the input to each of the two charge collection electrodes.

11. The sensor according to claim 8, wherein each pixel further comprises a reference electrode, located between the first and the second structures.

12. The sensor according to claim 8, wherein the at least one heating element comprises a heating element made of an electrically conducting material, located between the first and the second structures.

13. The sensor according to claim 1, wherein the at least one heating element comprises two heating elements made of an electrically conducting material, located on each side of a stack comprising the first and the second structures.

14. The sensor according to claim 13, wherein the heating elements of the different pixels together form heating strips distributed on each side of said stack, and arranged to be facing each other in pairs.

15. The sensor according to claim 1, wherein each pixel further comprises a glue portion, located between the first and the second structures.

16. The sensor according to claim 1, wherein the object to be imaged is a papillary print.

* * * * *